US006726619B2

(12) United States Patent
Gil Pascual

(10) Patent No.: US 6,726,619 B2
(45) Date of Patent: Apr. 27, 2004

(54) ARTIFICIAL INSEMINATION DEVICE FOR PIGS

(75) Inventor: Javier Gil Pascual, Barcelona (ES)

(73) Assignee: Iberica de Reproduccion Asistida, S.L., Barcelona (ES)

( * ) Notice: Subject to any disclaimer, the term of this patent is extended or adjusted under 35 U.S.C. 154(b) by 144 days.

(21) Appl. No.: 10/070,087

(22) PCT Filed: Dec. 29, 2000

(86) PCT No.: PCT/ES00/00499

§ 371 (c)(1), (2), (4) Date: Mar. 4, 2002

(87) PCT Pub. No.: WO01/49205

PCT Pub. Date: Jul. 12, 2001

(65) Prior Publication Data

US 2002/0151765 A1 Oct. 17, 2002

(30) Foreign Application Priority Data

Jan. 3, 2000 (ES) ........................................ 20000004 U
Sep. 29, 2000 (ES) ........................................ 200002360

(51) Int. Cl.$^7$ .............................. A61D 7/00; A61M 5/00
(52) U.S. Cl. ........................................ 600/35; 604/171
(58) Field of Search ............................ 600/35; 604/218, 604/275, 515, 906, 165.02, 203, 217, 167.01, 198, 227, 271, 530; 606/191, 193; 128/831

(56) References Cited

U.S. PATENT DOCUMENTS

| | | | | |
|---|---|---|---|---|
| 2,740,404 A | * | 4/1956 | Kohl | 604/167.01 |
| 4,136,695 A | * | 1/1979 | Dafoe | 128/831 |
| 4,173,227 A | * | 11/1979 | Cassou et al. | 604/218 |
| 4,178,936 A | | 12/1979 | Newcomb | 128/349 |
| 4,654,025 A | | 3/1987 | Cassou et al. | 604/55 |
| 5,195,979 A | | 3/1993 | Schinkel et al. | 604/164 |
| 5,389,089 A | * | 2/1995 | Bauer et al. | 604/271 |
| 5,496,272 A | * | 3/1996 | Chung et al. | 604/515 |
| 5,899,848 A | * | 5/1999 | Haubrich | 600/35 |

FOREIGN PATENT DOCUMENTS

| | | |
|---|---|---|
| EP | 0071538 | 2/1983 |
| EP | 0189702 | 6/1986 |
| FR | 2574656 | 6/1986 |

* cited by examiner

*Primary Examiner*—Eric F. Winakur
*Assistant Examiner*—Nikita R Veniaminov
(74) *Attorney, Agent, or Firm*—Baker Botts L.L.P.

(57) ABSTRACT

The device is equipped with the classical catheter (1) finishing in its front end in a tip (2) for attachment to the neck of the uterus, which is prolonged by a cannula (3) of smaller diameter. The device has said cannula (3) closed by means of an elongated lid (4'), with a rounded face, with a perimeter depression and concave curve (8) at the middle level, where orifices are established (5') as an outlet for the semen, specifically two orifices in diametric opposition, whose positioning is such that they are level with the uterine horns of the pig to be inseminated, by the introduction of the catheter (1), which is defined by a mark (11) in the cannula (3) or in a connector (12), which optimises the conditions of insemination allowing a lower semen consumption. In addition, the rear end of the lid (4') has a diameter after the cannula (3), to protect the edge of the free end from the latter, avoiding damage to the mucus of the female to be inseminated. In order to facilitate the process of application and to avoid contamination of the distal part of the cannula, this is presented divided into two portions that can be coupled together, the furthest away being introduced and therefore protected within the catheter (1).

11 Claims, 2 Drawing Sheets

ARTIFICIAL INSEMINATION DEVICE FOR PIGS

CROSS-REFERENCE TO RELATED APPLICATIONS

This is a national application based upon International Application No. PCT/ES00/00499, which was filed on Dec. 29, 2000 and which published in Spanish on Jul. 12, 2001, which in turn claims priority from Spanish Application No. U 200000004, which was filed on Jan. 3, 2001, and Spanish Application No. P200002360 filed on Sep. 29, 2000.

OBJECT OF THE INVENTION

The present invention relates to a device that is to constitute the means for transmission of a dose of semen from a recipient container to the uterus of a female pig, for the post-cervical artificial insemination thereof.

The object of the invention is to achieve a device with some optimum features, that not only facilitates the anatomic implantation thereof in the pig, prior to the insemination itself, but also determines some optimum results in said insemination, with a minimal consumption of semen, or what constitutes an optimum use of the sperm introduced by means of the device and the deposition in the uterine horn of the female pig herself, by means of outlets with which for such purposes the expulsion end of the device has been equipped.

BACKGROUND OF THE INVENTION

The application of the seminal dose in pigs on heat is performed normally by the vaginal route, using an instrument known as a catheter, this being made from a tubular implement, although it can present different forms. In all cases, it serves to reach the neck of the uterus and attach itself in the first 3–4 centimetres, as a nut does on a bolt, allowing the seminal dose to be applied through it, which has to pass through the rest of the uterine neck, approximately another 15 centimetres, before reaching the neck of the uterus.

There are currently different types of catheter that range from the classical reusable "Melrose" type made form a single rubber or similar piece that is very similar to the penis of the male pig, to an almost endless list of disposable plastic catheters.

These latter are generally formed of three pieces that correspond to the handle, the rod and the end or tip, such that the handle, not present in all catheters, is a piece of small dimensions that allows the catheter to be handled with ease and, for those that possess it, the cannula from the seminal container to be attached to the catheter.

The rod or body of the catheter is a tube approximately 50 centimetres long that acts as a conduct for the seminal liquid. The diameter of this tube is variable, although its outer diameter never exceeds 10 millimetres.

The point, as the main element of the catheter, is a piece of variable size and form which in any case allows the introduction and attachment to the neck of the uterus. They can take on cylindrical form (lid), made of foam and of a size near to 2 centimetres, and they can be conical, made of different types of plastic and with very variable sizes but which are usually between 3 and 8 centimetres. Attachment to the neck of the uterus is facilitated in some cases thanks to the helical form of the cone and in other cases thanks to the existence of rings or supplementary laminas that increase the degree of coupling between the catheter and the irregularities of the cervical wall.

In the French patent FR 8419723 a solution for a catheter is described, in which the terminal cannula does not emerge axially from the tip of the catheter, but rather does so laterally, such that said cannula, because of its inclined arrangement, impinges the wall of the uterine neck, which may produce scratching, and also makes handling difficult and uncomfortable.

In addition, in this Patent FR 8419723, it is specified that the cannula should have at least one lateral aperture, which suggests that the number of outlets is not determinant or important, inasmuch as in said Patent, the only thing that is foreseen is that the semen is introduced into the uterine neck, but with any orientation of outlet or outlets.

DESCRIPTION OF THE INVENTION

The artificial insemination device that is put forward is characterised in that inside the catheter a cannula is placed axially through which it is possible to achieve a post-cervical insemination, by lengthening the length of the insemination conduct beyond the uterine neck, depositing the semen in the uterine horns.

The new artificial insemination device consists of a standard catheter consisting of a tube or rod of flexible material and of a certain length, that has at its front end a standard tip, preferably cylindrical, with a widening spiral for attachment to the uterine neck. The back end of the catheter has a handle or a widening suitable for handling. The elements of the new invention consist of a hollow cannula suitable for post-cervical insemination. For this, the cannula is hollow, preferably of cylindrical form, whose outer diameter is particularly suitable to be introduced and housed, fitting tightly but allowing movement, inside the catheter. The cannula is obviously longer than the catheter, and is equipped at its rear end with a coupling device to allow bottles or tubes containing the semen to be introduced or the containers that contain it, directly if it is possible or with an intermediate adaptor. The front end of the cannula finishes in sphere or solid bead which closes it. A few centimetres from this sphere, the cannula's cross-section narrows gently, with two laterally opposite orifices to be found in said narrowing for expulsion of the semen.

In its use and functionality, in addition to the trans-cervical cannula, the insemination catheter requires a gynaecological lubricant, the way to proceed being as follows:

The vulva of the pig is cleaned carefully and the catheter is prepared to be introduced. Sufficient quantity of gynaecological gel should be applied to the tip of the catheter on the outside and inside of the outlet. Next, it is placed in position conventionally until the tip of the catheter is fixed to the uterine neck, attached to the first 3 or 4 centimetres, as is the case in traditional artificial insemination. Next, the trans-cervical cannula is introduced through the rear end of the catheter until coming into contact with the cervical rings. During this operation, the cannula impulses the gynaecological gel towards the inside of the neck of the uterus, activating the terminal ball of piston or plunger. This action is very important as, in this way, the gynaecological gel is deposited deep in the neck of the uterus to subsequently facilitate the advance of the cannula along its length to the body of the uterus. This is necessary as, in this fashion, as the cannula continues to be propelled through the catheter it ends up emerging on the outlet of the tip. Once the cannula emerges through the point of the catheter, the cannula is still pushed. The front end of the cannula, which has emerged through the point of the catheter, passes through the cervical rings until reaching the neck of the uterus. This advance of the front end of the cannula through the uterine neck is facilitated by the existence of the gynaecological gel previously impelled and the rounded form of the end of the cannula, thus avoiding possible damage or erosions in the mucus of the uterine neck. This additional distance advanced by the end of the cannula makes a better fertilisation possible. Next, the container with the seminal material is placed over the rear outlet of the cannula and the insemination performed. Once the seminal dose has been applied, the cannula is partially retracted. The set of the cannula and the catheter are then removed in conventional fashion.

The new invention confers important advantages, as it allows trans-cervical insemination with the semen deposited directly into the body of the uterus, instead of in the start of the uterine neck, as occurs conventionally, which requires that the sperm travel approximately 10 to 15 centimetres naturally until reaching the uterine body. The second advantageous point is the use made of the semen employed, as in the traditional procedure part of the semen deposited in the cervix may turn back, and be discharged from the vagina and therefore not used. According to the invention, the dose of semen to be used can be reduced, achieving an equally satisfactory use, with better yield of the sperm and genetic material used from the breeding male pigs.

The trans-cervical cannula is suitable for use in conjunction with any standard catheter or catheter already in existence, provided it has sufficient diameter and length in accordance with the needs, with the indispensable requirement that the tip of the catheter is opened frontally, in order that the cannula may emerge easily.

In an alternative form of embodiment, the lid of the cannula, instead of adopting a spherical configuration, adopts a lengthened configuration with a rounded end, with a perimeter groove and means in which the outlet orifices are precisely established, in twos and diametrically opposed. Said cannula, which will measure not less than 60 centimetres and not more than 75 centimetres, has in its end flow a connector by which the fastening connector will be attached to the seminal container.

In accordance with another of the characteristics of the invention, the rear end of said lid, basically of the screw type, is of larger diameter than the cannula to which it is attached, in order to totally cover the edge corresponding to the border or end of the latter, thus avoiding lesions due to friction with the uterine wall of the pig.

In accordance with another of the characteristics of the invention, it has been foreseen that said lid has specifically two outlet orifices, diametrically opposed to one another and which complementarily the connector or the cannula itself, for its entirety or part of its length, incorporates a signal that allows said orifices to be duly aligned in the uterus of the pig, specifically to bring them face to face with the respective uterine horns, which allows a considerable reduction in the seminal dose necessary to obtain satisfactory results from the insemination.

On the other hand, and from the point of view of maintaining the device sterile during the manipulation thereof, it has been foreseen that it is marketed in such a fashion that the front end of the cannula and thus also the end lid, are housed inside the helical tip, in order to keep them perfectly protected and so it is not necessary to perform any manipulation on them to thread the cannula through the inside of the tube or catheter.

To ensure that it is positioned in a stable fashion, it has in turn been foreseen that said tip has its front end closed, in order to avoid the accidental emergence of the cannula, and affected by at least one diametric cut to all its deformation and corresponding opening on applying axial pressure of an appropriate magnitude on the cannula.

This implies a greater emergence of the cannula at its other, rear, end; having anticipated for this and to make packaging easier, that said cannula can be fragmented into two sectors, that can be duly coupled at the moment of use of the equipment, one of them equipped to this effect with an inner casing coupled by pressure thereon and emerging to be coupled in analogous fashion to the other sector, with a suitable pressure to prevent accidental rotation of a sector with respect to the other from occurring and, as a result, the loss of marking for orientation of the front lid.

In this sense, it is also foreseen that either the two sectors of the cannula are related through a markedly Inclined plane that determines a single position relative to each other, which in substitution are related by an angular cut, with the same end, or by any other means that allows the relative position between the two sectors to be maintained.

DESCRIPTION OF THE DRAWINGS

In order to complete the description that is being carried out here and in order to facilitate a better understanding of the characteristics of the invention, in accordance with an example of a preferred practical embodiment thereof, said description is accompanied as an integral part thereof by a set of drawings in which, for illustrative purposes and in non-limiting fashion, the following has been represented.

PREFERRED EMBODIMENT OF THE INVENTION

Figures 1, 2:
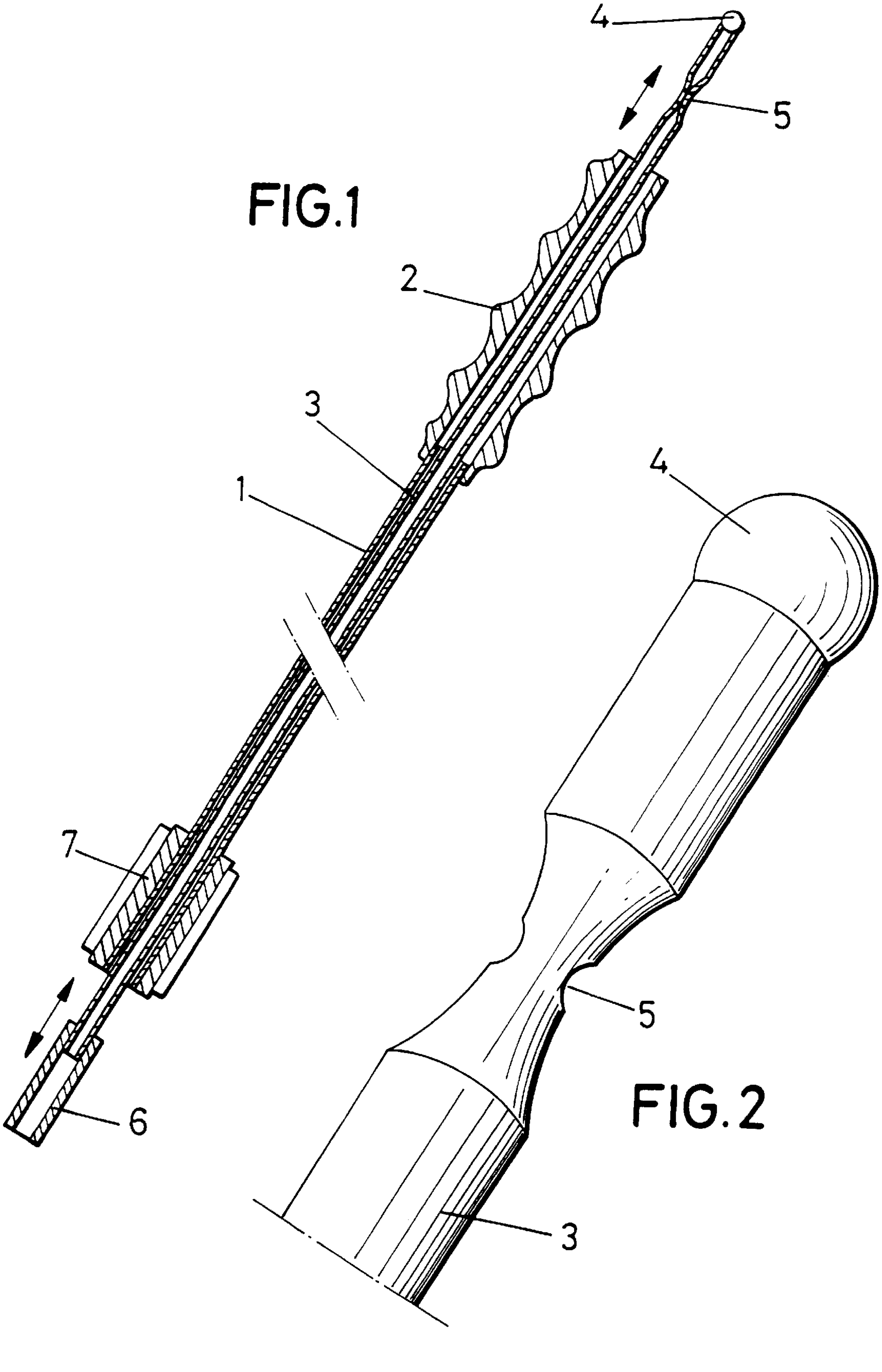
FIG. 1.—Shows a longitudinal section of the device performed in accordance with the objective of the invention, in which the cannula and the corresponding catheter can be clearly seen.
FIG. 2.—Shows detail in perspective and notably amplified of the front end of the cannula.

With respect to the embodiment represented in FIGS. 1 and 2, the post-cervical artificial insemination device for pigs comprises a catheter (1) consisting of a hollow tubular and flexible body, at one of whose ends there is a tip or front widening (2), preferably of conical form and determinant for a tip that can adopt a helical configuration or any other that improves attachment of the catheter to the neck of the uterus. Inside the tubular body (1) constituting the catheter there is a cannula (3), also tubular, the diameter of which is similar to the interior diameter of the body (1) of the catheter, the length of said cannula (3) being slightly longer than the length of the catheter that forms the tubular body (1) itself, the helical end (2) and a rear handle (7) equipped at the opposite end, a handle that is cylindrical , or with any other suitable configuration, determining a piece of small dimensions for its attachment. The front end of the cannula (3) finishes in a sphere (4) acting as a lid, the diameter of which is approximately equal to that of the cannula itself (3) or slightly greater, such that at short distance from said sphere (4) the cannula (3) has a curved and gentle narrowing of diameter, two orifices (5) being found in the zone of minimum diameter, diametrically opposed to one another, that connect the inside of the cannula (3) with the outside.

The opposite end of the cannula (3) has an outlet (6) to which can be coupled a container containing the semen and adaptor for use.

Figure 3:
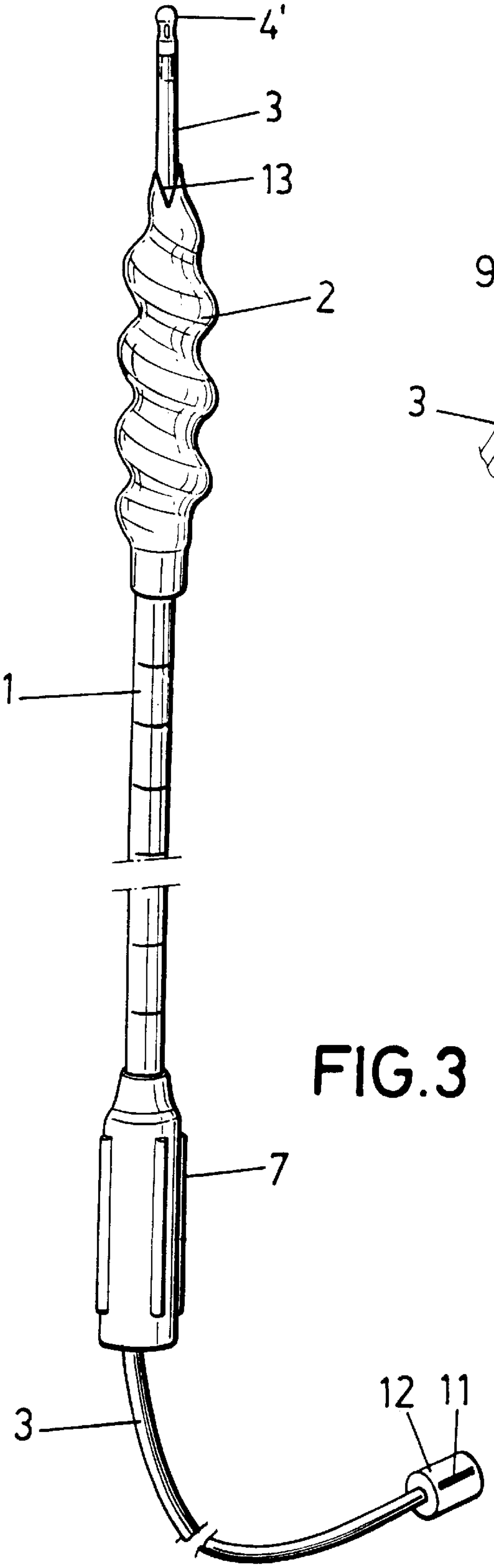
FIG. 3.—Shows a representation of the side elevation of the artificial insemination device according to an alternative or variant of the embodiment with respect to that show in FIGS. 1 and 2.
Figure 4:
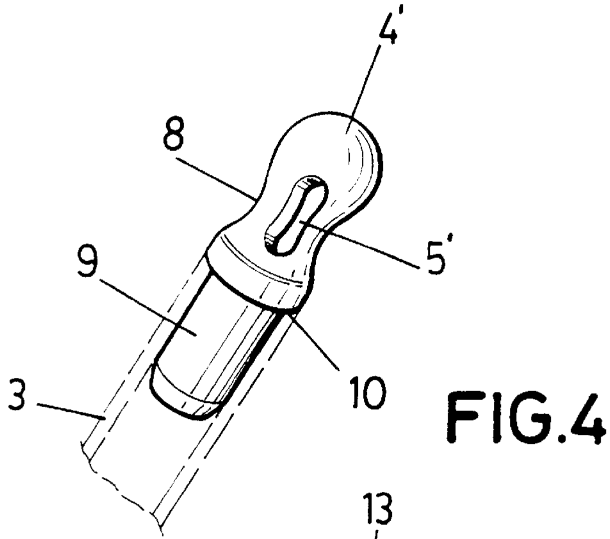
FIG. 4.—Shows amplified detail in perspective of the front lid in which the prolongation of the tip of the catheter finishes, corresponding to the embodiment of the previous figure.

In an alternative embodiment represented in FIGS. 3 to 6, it can be seen that the lid which the cannula finishes as, referenced in this case with (4'), has a slightly elongated configuration, being of screw type and presenting a perimeter groove and concave curve (8) in its mid zone, such that in this groove (8) are established two side orifices (5'), diametrically opposed to one another, that allow outflow of the semen, this lid (4') being prolonged into a subsequent neck (9) for insertion of the end of the cannula (3), with the particular characteristic that a step (10) defined between the lid itself (4') and the neck (9) is such that that the subsequent diameter of said lid is greater than the diameter of the cannula (3), as shown specifically in FIG. 4, all this with the aim of appropriately protecting the edge corresponding to the free end of the cannula (3) and avoiding harmful actions of said edge on the mucus of the pig.

With the specific number and arrangement of the orifices (5') for the outflow of semen, collaborates a mark (11) established in the connector (12) or in all the part of the length of the cannula (3), as is observed in FIG. 3, allowing the inseminator to perfectly orient the aforementioned orifices (5') towards the uterine horns, when introduction of the catheter (1) has been completed, as when said mark (11) is perfectly oriented upwards, it is certain that the orifices (5') are oriented laterally.

All these structural characteristics of the catheter ensure that, compared to the classical seminal dosing in which the order of three thousand million spermatozoids are needed, with the catheter of the invention, a doses of just five hundred million spermatozoids will be necessary, or even less, but with some optimum results of the insemination guaranteed.

Figure 5:
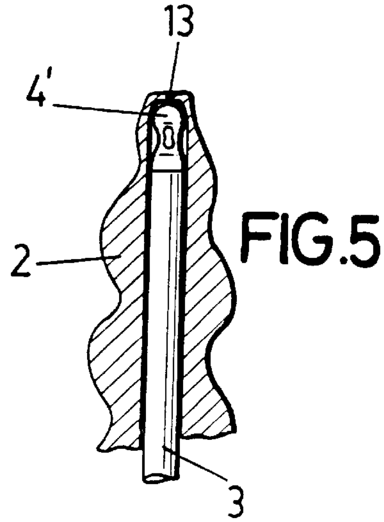
FIG. 5.—Shows partial detail, amplified and in transversal section, of the front end of the helical tip, in an inoperative situation for the device, in which the end front of the cannula is housed inside said tip.

During commercial distribution of the device and to appropriately protect both the lid and the frontal or back zone of the cannula from manipulations that might give rise to contamination during such a manipulation, it has been foreseen that, as is represented in FIG. 5, the cannula (3), axially movable both within the rod or tubular body (1) of the catheter and of the helical tip (2), is housed inside the latter, in addition to being appropriately stabilised, to which effect the frontal end of said tip (2) is initially closed and equipped with at least a diametric cut or an opening (13) that, when axial pressure of an appropriate magnitude is exerted with the cannula (3), once the tip has been introduced into the neck of the uterus of the pig, allows the deformation and subsequent opening for emergence of the cannula (3) with its lid (4').

Figure 6:
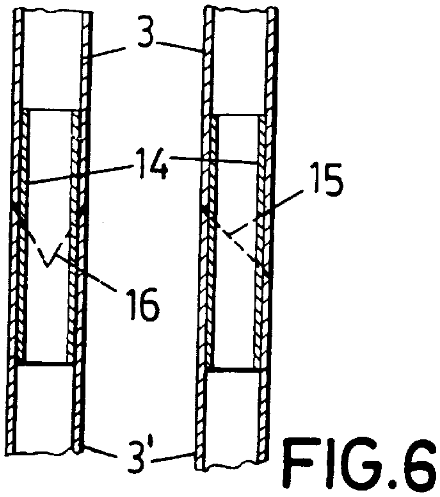
FIG. 6.—Shows, finally, two of the possible practical embodiments for coupling the two sectors of the cannula, according to respective side projection views and corresponding to the variant of embodiment represented in FIGS. 3, 4 and 5.

On the other hand, and given the considerable length of the cannula (3), it has been foreseen that to facilitate the handling at the time of application, the cannula (3) can be fragmented into two sectors, as is indicated in FIG. 6, setting both sectors (3–3') to each other by means of an inner casing (14), of considerable length, one of whose two halves is coupled by pressure to one of the sectors (3), while the other half can be plugged, also by applying pressure, into the second sector (3'), which allows easy assembly of the two sectors of the cannula (3) at the moment when the device is used.

In order that this bipartite character of the cannula (3) does not influence the aforementioned marking (11), which can be established on the connector itself (12) for the semen container or be located over the side wall of the cannula itself, without this needing to affect the two sectors thereof, said sectors (3–3') can be connected to each other by means of a bevel (15) as shown in the broken line in the detail on the right of FIG. 6, or by means of a cut at an angle (16) also represented by a broken line on the left drawing of this FIG. 6, within another broad range of possibilities to this effect, in order to establish in any case a relative predetermined position for assembly of the two sectors (3–3').

What is claimed is:

1. A device for artificial insemination of pigs comprising:

a catheter having a front end and a rear end, the catheter comprising a tubular elongated flexible element;

a widening tip at the front end of the catheter, the widening tip being helical with respect to a side surface thereof;

a tubular element at the rear end of the catheter, the tubular element of larger diameter than the catheter and having a handle for support; and a cannula within the tubular elongated flexible element of the catheter, the cannula being capable of being longitudinally fixed to the inside of the tubular elongated flexible element of the catheter with a tight fit, the cannula being capable of emerging through a first outlet that serves as the rear end of the catheter, the cannula having a front end in the shape of a sphere or rounded point, the diameter of which is approximately equal to or slightly greater than the diameter of the cannula and approximately equal to or less than the diameter of the inside of the tubular elongated flexible element of the catheter, the sphere or rounded point acting as a lid for closing the front end of the cannula and being suitable for movement along the length of the uterine neck of the pig until the uterine horns without eroding or damaging the mucus of the pig, wherein, at a short distance away from the lid there is a gentle narrowing of the diameter of the cannula, forming a depression in which there are two lateral orifices that connect the inside of the cannula with the outside, equipped for depositing semen into the body of the uterus of the pig to be inseminated.

2. The device of claim 1, further comprising a second outlet suitable for receiving tubes containing semen at a rear end of the cannula, the semen being stored directly or by an intermediate adaptor, wherein, the length of the cannula is longer than the combined length of the tubular elongated flexible element of the catheter, the widening tip, and the handle, the length of the cannula is sufficient so that the cannula when introduced to a maximum extension in the pig is suitable for reaching the uterine body of the pig, and the lid is suitable for adjusting the inner diameter of the tubular elongated flexible element of the catheter, the sphere or rounded point serving as a lid being able to push a gynecological gel deposited previously in side the widening tip of the catheter to the uterine neck during the process of in semination.

3. The device of claim 2, wherein the dimensions of the cannula permit its use with any standard tubular catheter equipped with a frontal outlet orifice at the front end of the catheter, the cannula being able to present a front section thereof affected by a frontal or lateral aperture.

4. The device of claim 1, wherein the dimensions of the cannula permit its use with any standard tubular catheter equipped with a frontal outlet orifice at the front end of the catheter, the cannula being able to present a front section thereof affected by a frontal or lateral aperture.

5. A device for artificial insemination of pigs comprising:

a catheter having a front end and a rear end, the catheter including a tubular elongated flexible element;

an widening tip at the front end of the catheter, the widening tip being helical with respect to a side surface thereof;

a tubular element at the rear end of the catheter, the tubular element of larger diameter than the catheter and having a handle for support; and a cannula within the tubular elongated flexible element of the catheter, the cannula being capable of being longitudinally fixed to the inside of the tubular elongated flexible element of the catheter with a tight fit, the cannula being capable of emerging through a first outlet that serves as the rear end of the catheter, the cannula having a front end in the shape of a sphere or rounded point, the diameter of which is approximately equal to or slightly greater than the diameter of the cannula and approximately equal to or less than the diameter of the inside of the tubular elongated flexible element of the catheter, the sphere or rounded point acting as a lid for closing the front end of the cannula and being suitable for movement along the length of the uterine neck of the pig until the uterine horns without eroding or damaging the mucus of the pig, wherein, the lid has a rear end and a middle area, the lid is capable of being materialized in a screw body, the lid being slightly elongated, the lid having a perimeter depression, the lid having a concave curve at the middle area, the lid having outlet orifices established for the semen, and the rear end of the lid has a diameter slightly greater than that of the cannula, the rear end being coupled by a classical neck, such that the edge corresponding to a front section of the cannula is covered and protected by the widening of the rear end of the lid.

6. The device of claim 5, wherein, the outlet orifices of the lid are two in number and are diametrically opposed to one another, and the handle or the cannula incorporates a signal that, duly related to the position of the two outlet orifices, permits after coupling of the catheter that an inseminator can orient the two outlet orifices for semen out towards the uterine horns of the pig to be inseminated.

7. The device of claim 6, wherein the widening tip has a closed frontal end and at least one diametric opening or cut, the at least one diametric opening or cut permitting the opening of the closed frontal end of the widening tip by deformation, the closed frontal end of the widening tip being capable of maintaining the front end of the cannula with the lid housed inside the widening tip during manipulation of the device and until the widening tip is housed in the neck of the uterus of the pig to be inseminated.

8. The device of claim 7, wherein the cannula is fragmented into a first sector and a second sector, the sectors being capable of being coupled with the collaboration of a casing, the casing being coupled under pressure to the first sector, the sectors being connected between each other by a bevel, a “V” cut, or another manner that determines a relative fixed and pre-established position between the first and second sectors and that maintains a mark established on the cannula or on a connector operational in which the cannula then finishes.

9. The device of claim 6, wherein the cannula is fragmented into a first sector and a second sector, the sectors being capable of being coupled with the collaboration of a casing, the casing being coupled under pressure to the first sector, the sectors being connected between each other by a bevel, a “V” cut, or another manner that determines a relative fixed and pre-established position between the first and second sectors and that maintains a mark established on the cannula or on a connector operational in which the cannula then finishes.

10. The device of claim 5, wherein the widening tip has a closed frontal end and at least one diametric opening or cut, the at least one diametric opening or cut permitting the opening of the closed frontal end of the widening tip by deformation, the closed frontal end of the widening tip being capable of maintaining the front end of the cannula with the lid housed inside the widening tip during manipulation of the device and until the widening tip is housed in the neck of the uterus of the pig to be inseminated.

11. The device of claim 10, wherein the cannula is fragmented in to a first sector and a second sector, the sectors being capable of being coupled with the collaboration of a casing, the casing being coupled under pressure to the first sector, the sectors being connected between each other by a bevel, a “V” cut, or another manner that determines a relative fixed and pre-established position between the first and second sectors and that maintains a mark established on the cannula or on a connector operational in which the cannula then finishes.

* * * * *